United States Patent
Pommier et al.

(10) Patent No.: US 8,716,295 B2
(45) Date of Patent: May 6, 2014

(54) FLUOROQUINOLONE DERIVATIVES OR SULFONAMIDE MOIETY-CONTAINING COMPOUNDS AS INHIBITORS OF TYROSYL-DNAPHOSPHODIESTERASE (TDP1)

(76) Inventors: Yves Pommier, Bethesda, MD (US); Christophe Marchand, Silver Spring, MD (US); Periyasamy Selvam, Kerala (IN); Thomas Dexheimer, Montgomery Village, MD (US); Kasthuraiah Maddali, Rockville, MD (US)

( * ) Notice: Subject to any disclaimer, the term of this patent is extended or adjusted under 35 U.S.C. 154(b) by 0 days.

(21) Appl. No.: 13/283,282

(22) Filed: Oct. 27, 2011

(65) Prior Publication Data

US 2012/0172371 A1 Jul. 5, 2012

Related U.S. Application Data

(60) Provisional application No. 61/407,325, filed on Oct. 27, 2010.

(51) Int. Cl.
| | |
|---|---|
| *A61K 31/4745* | (2006.01) |
| *A61K 31/496* | (2006.01) |
| *A61K 31/505* | (2006.01) |
| *A61K 31/506* | (2006.01) |
| *A61K 45/06* | (2006.01) |
| *C12N 9/99* | (2006.01) |

(52) U.S. Cl.
USPC ............... 514/252.18; 514/253.08; 514/275; 435/184

(58) Field of Classification Search
USPC ............... 514/252.18, 253.08, 275; 435/184
See application file for complete search history.

(56) References Cited

U.S. PATENT DOCUMENTS

| | | |
|---|---|---|
| 2003/0105053 A1 | 6/2003 | Burgin, Jr. et al. |
| 2003/0124587 A1 | 7/2003 | Kan et al. |

FOREIGN PATENT DOCUMENTS

| | | |
|---|---|---|
| WO | WO 2006/099095 | 9/2006 |
| WO | WO 2007/112121 | 10/2007 |
| WO | WO 2007/126857 | 11/2007 |
| WO | WO 2008/124145 | 10/2008 |

OTHER PUBLICATIONS

Antony et al., "Novel high-throughput electrochemiluminescent assay for identification of human tyrosyl-DNA phosphodiesterase (Tdp1) inhibitors and characterization of furamidine (NSC 305831) as an inhibitor of Tdp1," *Nucleic Acids Res.* 35(13):4474-4484, 2007.
Barthelmes et al., "TDP1 Overexpression in Human Cells Counteracts DNA Damage Mediated by Topoisomerases I and II," *J. Biol. Chem.* 279:55618-55625, 2004.
Cheng et al., "Kinetic Studies of Human Tyrosyl-DNA Phosphodiesterase, an Enzyme in the Topoisomerase I DNA Repair Pathway," *Eur. J. Biochem.* 269:3697-3704, 2002.
Connelly and Leach, "Repair of DNA covalently linked to protein," *Mol Cell* 13(3):307-316, 2004.

(Continued)

*Primary Examiner* — Savitha Rao
(74) *Attorney, Agent, or Firm* — Klarquist Sparkman LLP (57) ABSTRACT

A method for treating cancer in a subject, comprising administering to a subject having cancer a therapeutically effective amount of (i) a fluoroquinolone derivative that inhibits tyrosyl-DNA-phosphodiesterase 1 (Tdp1) activity or (ii) a sulfonamide moiety-containing compound that inhibits tyrosyl-DNA-phosphodiesterase 1 (Tdp1) activity, thereby treating the cancer in the subject. In certain embodiments, the fluoroquinolone derivative or sulfonamide moiety-containing compound is co-administered with a topoisomerase I (TopI) inhibitor.

11 Claims, 3 Drawing Sheets

(56) References Cited

OTHER PUBLICATIONS

Davies et al., "The Crystal Structure of Human Tyrosyl-DNA Phosphodiesterase, Tdp1," *Structure* 10:237-248, 2002. (Abstract Only).
Davies et al., "Crystal Structure of a Transition State Mimic for Tdp1 Assembled from Vanadate, DNA, and a Topoisomerase I-Derived Peptide," *Chem. Biol.* 10:139-147, 2003, (Abstract Only).
Davies et al., "Explorations of Peptide and Oligonucleotide Binding Sites of Tyrosyl-DNA Phosphodiesterase Using Vanadate Complexes," *J. Med. Chem.* 47:829-837, 2004. (Abstract Only).
de Almeida et al., "Synthesis and antitubercular activity of lipophilic moxifloxacin and gatifloxacin derivatives," *Bioorganic & medicinal chemistry letters* 17(20):5661-5664, 2007. (Abstract Only).
Debéthune et al., "Processing of Nucleopeptides Mimicking the Topoisomerase I-DNA Covalent Complex by Tyrosyl-DNA Phosphodiesterase," *Nucleic Acids Res.* 30(5):1198-1204, 2002.
Dexheimer et al., "Tyrosyl-DNA phosphodiesterase as a target for anticancer therapy," *Anticancer Agents Med Chem.* 8(4):381-389, 2008.
Dexheimer et al., "4-Pregnen-21-ol-3,20-dione-21-(4-bromobenzenesulfonate) (NSC 88915) and related novel steroid derivatives as tyrosyl-DNA phosphodiesterase (Tdp1) inhibitors," *J Med Chem.* 52(22):7122-7131, 2009.
Herold et al., "Ciprofloxacin induces apoptosis and inhibits proliferation of human colorectal carcinoma cells," *British Journal of Cancer* 86:443-448, 2002.
Hu, "Neomycin inhibits angiogenin-induced angiogenesis," *PNAS* 95:9791-9795, 1998.
Interthal et al., "The Tyrosyl-DNA Phosphodiesterase Tdp1 is a member of the phospholipase D superfamily," *PNAS* 90(21):12009-12014, 2001.
Liao et al., "Inhibition of human tyrosyl-DNA phosphodiesterase by aminoglycoside antibiotics and ribosome inhibitors," *Mol Pharmacol.* 70(1):366-372, 2006.
Liu et al., "Repair of Topoisomerase I Covalent Complexes in the Absence of the Tyrosyl-DNA Phosphodiesterase Tdp1," *PNAS* 99:14970-14975, 2002.
Marchand et al., "Identification of phosphotyrosine mimetic inhibitors of human tyrosyl-DNA phosphodiesterase I by a novel AlphaScreen high-throughput assay," *Mol Cancer Ther.* 8(1):240-248, 2009.
Meng et al., "Non-Camptothecin DNA Topoisomerase I Inhibitors in Cancer Therapy," *Curr. Top. Med. Chem.* 3:305-320, 2003. (Abstract only).
Mondal et al., "Comparative evaluation of antiproliferative activity and induction of apoptosis by some fluoroquinolones with a human non-small cell lung cancer cell line in culture," *Asian Pacific journal of cancer prevention* 5(2):196-204, 2004. (Abstract only).
Plo et al., "Association of XRCC1 and Tyrosyl DNA Phosphodiesterase (Tdp1) for Repair of Topoisomerase I-Mediated DNA Lesions," *DNA Repair* 2:1087-1100, 2003. (Abstract only).
Pommier, "Camptothecins and Topoisomerase I: A Foot in the Door. Targeting the Genome Beyond Topoisomerase I with Camptothecins and Novel Anticancer Drugs: Importance of DNA Replication, Repair and Cell Cycle Checkpoints," *Curr. Med. Chem.—Anti-Cancer Agents* 4:429-434, 2004.
Pommier et al., "DNA topoisomerases and their poisoning by anticancer and antibacterial drugs," *Chem Biol.* 17(5):421-433, 2010. (Abstract only).
Pouliot et al., "Yeast Gene for a Tyr-DNA Phosphodiesterase that Repairs Topoisomerase I Complexes," *Science* 286:552-555, 1999.
Pouliot et al., "Pathways for repair of topoisomerase I covalent complexes in *Saccharomyces cerevisiae*," *Genes to Cells* 6:667-687, 2001.
Raykov et al., "Anticancer effects of an oncolytic parvovirus combined with non-conventional therapeutics on pancreatic carcinoma cell lines," *J. Acta virologica*, 53(1):57-60, 2009. (Abstract only).
Selvam et al., "Pharmacological Screening of Some Novel Isatin Derivatives," *Indian Journal of Pharmaceutical Sciences* 465-469, Jul.-Aug. 2004.
Selvam et al., "Anti-influenza virus activities of 4-[(1,2-dihydro-2-oxo-3H-indol-3-ylidene)amino]-N-(4,6-dimethyl-2-pyrimidin-2-yl)benzenesulphonaminde and its derivatives," *Antiviral Chemistry & Chemotherapy* 17:269-274, 2006.
Selvam et al., "Inhibitory activity of 4-[(1,2-dihydro-2-oxo-3H-indol-3-ylidene)amino]-N-(4,6-dimethylpyrimidin-2-yl)benzenesulphonamide and its derivatives against orthopoxvirus replication in vitro," *Antiviral Chemistry & Chemotherapy* 17:107-110, 2006.
Selvam et al., "Synthesis and Antiviral Studies of Novel N-Sulphonamidomethyl piperazinyl Fluoroquinolones," *Indian Pharm Sci.* 71(4):432-436, 2009.
Selvam et al., "Activity of isatine-sulfadimidine derivatives against 2009 pandemic H1N1 influenza virus in cell culture," *Antiviral Chemistry & Chemotherapy* 20:143-146, 2010.
Weidlich et al., "Inhibitors of human tyrosyl-DNA phospodiesterase (hTdp1) developed by virtual screening using ligand-based pharmacophores," *Bioorg Med Chem.* 8(1):182-189, Epub Nov. 11, 2009. (Abstract only).

| Name | R$_1$ | R$_2$ | R$_3$ | R$_4$ | IC$_{50}$ (µM) |
|---|---|---|---|---|---|
| Ciprofloxacin | cyclopropyl | H | H | H | >333 |
| CF-SA | cyclopropyl | H | H | HN-C$_6$H$_4$-SO$_2$NH$_2$ | NA |
| CF-SD | cyclopropyl | H | H | HN-C$_6$H$_4$-SO$_2$-NH-pyrimidinyl | 0.237±0.092 (n=3) |
| CF-SDM | cyclopropyl | H | H | HN-C$_6$H$_4$-SO$_2$-NH-(4,6-dimethylpyrimidinyl) | 0.163±0.063 (n=4) |
| Gatifloxacin | cyclopropyl | -OCH$_3$ | -CH$_3$ | H | >333 |
| GF-SA | cyclopropyl | -OCH$_3$ | -CH$_3$ | HN-C$_6$H$_4$-SO$_2$NH$_2$ | >333 |
| GF-SD | cyclopropyl | -OCH$_3$ | -CH$_3$ | HN-C$_6$H$_4$-SO$_2$-NH-pyrimidinyl | 0.197±0.041 (n=3) |
| GF-SDM | cyclopropyl | -OCH$_3$ | -CH$_3$ | HN-C$_6$H$_4$-SO$_2$-NH-(4,6-dimethylpyrimidinyl) | 0.022±0.009 (n=4) |
| Norfloxacin | ethyl | H | H | H | >333 |
| NF-SA | ethyl | H | H | HN-C$_6$H$_4$-SO$_2$NH$_2$ | >333 |
| NF-SD | ethyl | H | H | HN-C$_6$H$_4$-SO$_2$-NH-pyrimidinyl | 1.590±0.291 (n=3) |
| NF-SDM | ethyl | H | H | HN-C$_6$H$_4$-SO$_2$-NH-(4,6-dimethylpyrimidinyl) | 0.005±0.002 (n=4) |

Table 1: Structures and IC$_{50}$ values

FLUOROQUINOLONE DERIVATIVES OR SULFONAMIDE MOIETY-CONTAINING COMPOUNDS AS INHIBITORS OF TYROSYL-DNAPHOSPHODIESTERASE (TDP1)

CROSS-REFERENCE TO RELATED APPLICATION

This application claims the benefit of U.S. Provisional Application No. 61/407,325, filed Oct. 27, 2010, which is incorporated by reference herein in its entirety.

BACKGROUND

Chemotherapy can provide a therapeutic benefit in many cancer subjects, but it often ultimately fails to cure the disease because cancer cells can become resistant to the chemotherapeutic agent. To overcome these limitations additional antineoplastic strategies are needed, such as the use of potentiating agents that restore or amplify the effect of antitumor agents. Such amplification agents could also permit lower doses of cytotoxic drugs to be used, which could help minimize unwanted side-effects of the cytotoxic drugs.

Tyrosyl-DNA phosphodiesterase 1 (Tdp1) acts in the Topoisomerase I (TopI) pathway to counteract the anticancer activity of TopI inhibitors and promote tumor resistance of chemotherapeutic drugs. In particular, Tdp1 is a DNA repair enzyme that is involved in the repair of DNA lesions that are created when the activity of TopI is inhibited, for example by TopI inhibitors that have anticancer activity. Tdp1 is an enzyme that catalyzes the hydrolysis of 3'-phosphotyrosyl bonds. Such linkages form in vivo following the DNA processing activity of TopI. For this reason, Tdp1 has been implicated in the repair of irreversible TopI-DNA covalent complexes, which can be generated by either exogenous or endogenous factors. Tdp1 has been regarded as a potential therapeutic co-target of TopI in that it seemingly counteracts the effects of TopI inhibitors, such as camptothecin. Thus, by reducing the repair of TopI-DNA lesions, Tdp1 inhibitors have the potential to augment the anticancer activity of TopI inhibitors.

SUMMARY

Disclosed herein is a method for treating cancer in a subject, comprising administering to a subject having cancer a therapeutically effective amount of a topoisomerase I (TopI) inhibitor and a therapeutically effective amount of a fluoroquinolone derivative that inhibits tyrosyl-DNA-phosphodiesterase 1 (Tdp1) activity, thereby treating the cancer in the subject.

Also provided herein is a method for treating cancer in a subject, comprising administering to a subject having cancer a therapeutically effective amount of a fluoroquinolone derivative that inhibits tyrosyl-DNA-phosphodiesterase 1 (Tdp1) activity, thereby treating the cancer in the subject.

Further disclosed is a method for inhibiting tyrosyl-DNA-phosphodiesterase 1 (Tdp1) activity in a biological sample with Tdp1 activity, comprising contacting the biological sample with a fluoroquinolone derivative that inhibits Tdp1 activity, thereby inhibiting Tdp1 activity.

A pharmaceutical composition also is described herein that includes a therapeutically effective amount of a TopI inhibitor and a therapeutically effective amount of a fluoroquinolone derivative that inhibits Tdp1 activity.

In a further aspect, there is disclosed herein a method for treating cancer in a subject, comprising administering to a subject having cancer a therapeutically effective amount of a topoisomerase I (TopI) inhibitor and a therapeutically effective amount of a sulfonamide moiety-containing compound that inhibits tyrosyl-DNA-phosphodiesterase 1 (Tdp1) activity, thereby treating the cancer in the subject.

Also provided herein is a method for treating cancer in a subject, comprising administering to a subject having cancer a therapeutically effective amount of a sulfonamide moiety-containing compound that inhibits tyrosyl-DNA-phosphodiesterase 1 (Tdp1) activity, thereby treating the cancer in the subject.

Further disclosed is a method for inhibiting tyrosyl-DNA-phosphodiesterase 1 (Tdp1) activity in a biological sample with Tdp1 activity, comprising contacting the biological sample with a sulfonamide moiety-containing compound that inhibits Tdp1 activity, thereby inhibiting Tdp1 activity.

A pharmaceutical composition also is described herein that includes a therapeutically effective amount of a TopI inhibitor and a therapeutically effective amount of a sulfonamide moiety-containing compound that inhibits Tdp1 activity.

The foregoing will become more apparent from the following detailed description, which proceeds with reference to the accompanying figures.

DETAILED DESCRIPTION

As used herein, the singular terms "a," "an," and "the" include plural referents unless context clearly indicates otherwise. Also, as used herein, the term "comprises" means "includes."

To facilitate review of the various examples of this disclosure, the following explanations of specific terms are provided:

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

The term "alkoxy" refers to a group of the formula —OR, wherein R is an organic group such as an alkyl group, optionally substituted with an alkenyl, alkynyl, aryl, aralkyl, cycloalkyl, halogenated alkyl, or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Alkyl groups may be substituted alkyls wherein one or more hydrogen atoms are substituted with a substituent such as halogen, cycloalkyl, alkoxy, amino, hydroxyl, aryl, or carboxyl. For example, an "alkoxyalkyl" has the structure —ROR, wherein R is an alkyl group.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "co-administration" or "co-administering" refers to administration of the compound disclosed herein with at least one other therapeutic agent within the same general time period, and does not require administration at the same exact moment in time (although co-administration is inclusive of administering at the same exact moment in time). Thus, co-administration may be on the same day or on different days, or in the same week or in different weeks.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

"Derivative" refers to a compound or portion of a compound that is derived from or is theoretically derivable from a parent compound. However, a "fluoroquinolone derivative" is not necessarily synthesized from a starting compound that is a fluoroquinolone.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

"Nanomolar inhibitor" or "nanomolar concentration" refers to an $IC_{50}$ of less than 1.0 µM.

The term "neoplasm" refers to an abnormal cellular proliferation, which includes benign and malignant tumors, as well as other proliferative disorders.

The term "subject" includes both human and veterinary subjects.

The term "pharmaceutically acceptable salt or ester" refers to salts or esters prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977). "Pharmaceutically acceptable esters" includes those derived from compounds described herein that are modified to include a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$ alkoxymethyl esters for example methoxy-methyl, $C_{1-6}$ alkanoyloxymethyl esters for example pivaloyloxymethyl, phthalidyl esters, $C_{3-8}$ cycloalkoxycarbonyloxy$C_{1-6}$ alkyl esters for example 1-cyclohexylcarbonyloxyethyl; 1,3-dioxolen-2-onylmethyl esters for example 5-methyl-1,3-dioxolen-2-onylmethyl; and $C_{1-6}$ alkoxycarbonyloxyethyl esters for example 1-methoxycarbonyl-oxyethyl which may be formed at any carboxy group in the compounds.

An in vivo hydrolysable ester containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds are those wherein the counter-ion is pharmaceutically acceptable.

However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The term "prodrug" also is intended to include any covalently bonded carriers that release a disclosed compound or a parent thereof in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently claimed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. In particular, ester prodrugs are specifically contemplated herein. Similarly, prodrugs include compounds having an amino or sulfhydryl group functionalized with any group that is cleaved to yield the corresponding free amino or free sulfhydryl group. Examples of prodrugs include, without limitation, compounds having a hydroxy, amino and/or sulfhydryl group acylated with an acetate, formate, or benzoate group.

Protected derivatives of the disclosed compounds also are contemplated. The term "protecting group" or "blocking group" refers to any group that when bound to a functional group prevents or diminishes the group's susceptibility to reaction. "Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. The terms "deprotecting," "deprotected," or "deprotect," as used herein, are meant to refer to the process of removing a protecting group from a compound.

A "therapeutically effective amount" or "diagnostically effective amount" refers to a quantity of a specified agent sufficient to achieve a desired effect in a subject being treated with that agent. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease or condition, for example, in a subject who is at risk for a disease such as cancer, particularly a metastatic cancer. A "prophylactic" treatment is a treatment administered to a subject who does not exhibit signs of a disease or exhibits only early signs for the purpose of decreasing the risk of developing pathology.

The terms "tyrosyl-DNA phosphodiesterase" and "Tdp" refer to a protein that is encoded by a tyrosine-DNA phosphodiesterase gene sequence or to a protein. In addition, the terms refer to enzymes that cleave the phosphodiester bond linking the active site tyrosine residue of topoisomerase I with 3'-terminus of DNA in topo I-DNA complexes Particular examples of the presently disclosed agents include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Fluoroquinolone Compounds

Figure 1:
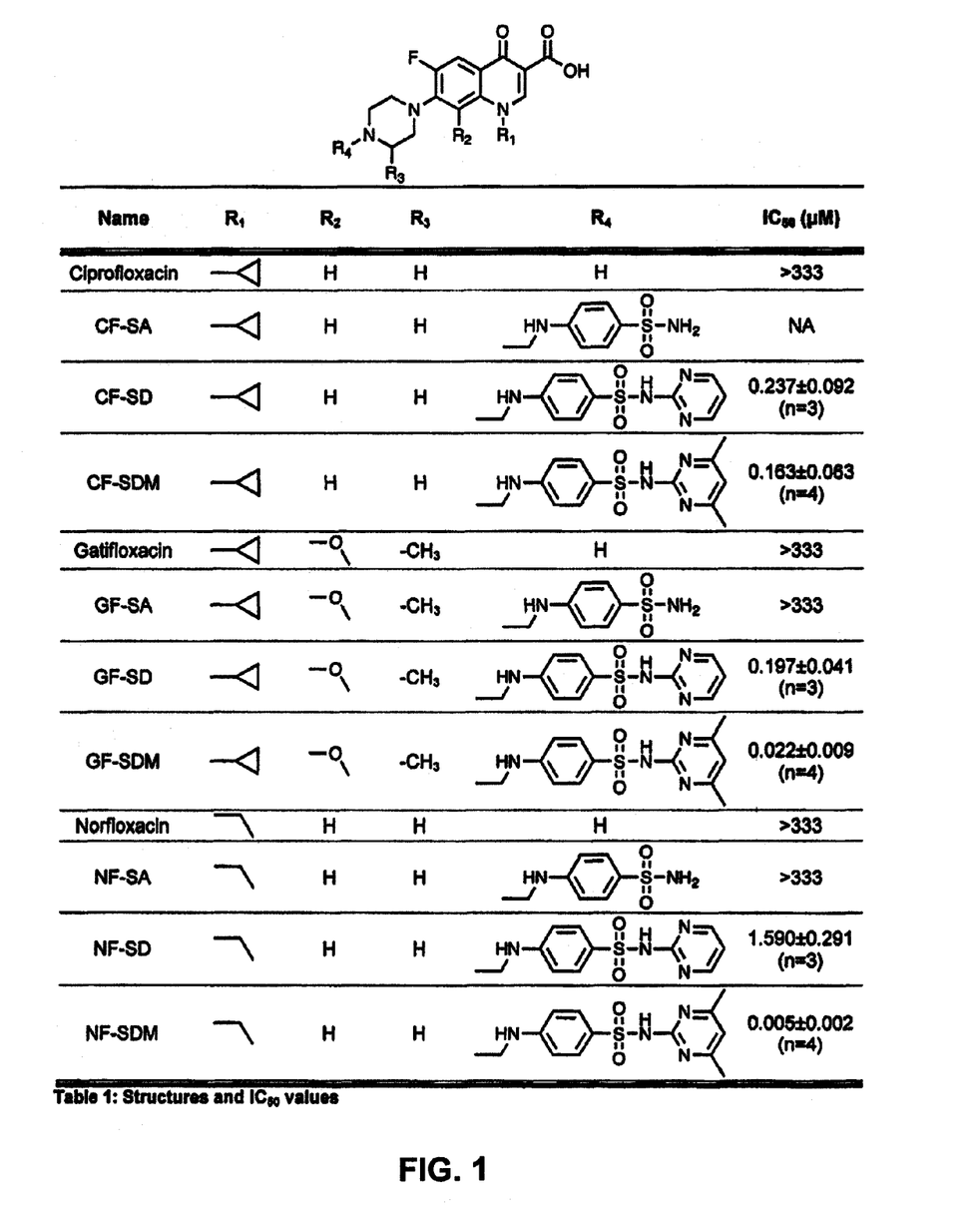
FIG. 1 depicts fluoroquinolone compound structures and their respective $IC_{50}$ Tdp1 inhibition results.

The compounds disclosed herein are capable of modulating the activity of tyrosyl-DNA phosphodiesterases (Tdps), particularly tyrosyl-DNA phosphodiesterase 1 (Tdp1). It has been discovered that certain fluoroquinolone derivatives, for example GF-SDM and NF-SDM as described below, inhibit the activity of Tdp1 in the nanomolar range. The two most effective fluoroquinolone derivatives, GF-SDM and NF-SDM, both contain a sulfadimidine moiety. While not as effective as the fluoroquinolone derivatives containing a sulfadimidine moiety it has also been discovered that fluoroquinolone derivatives containing a sulfadiazine moiety also show inhibitory activity. The fluoroquinolone derivatives that include a sulfadimidine moiety or a sulfadiazine moiety are potent inhibitors of Tdp1's ability to hydrolyze the phosphodiester bond between a tyrosine residue and a DNA 3'-phosphate. The sulfadimidine moiety and the sulfadiazine moiety differ by the presence of a methyl group on the heterocyclic ring. Fluoroquinolone derivatives that did not include this heterocyclic ring did not have inhibitory activity (see Table 1, NF-SA and CF-SA). Thus, it appears that the presence of the heterocyclic ring present in both the sulfadimidine moiety and sulfadiazine moiety is at least partially responsible for the inhibitory activity of these derivatives. Because these fluoroquinolone derivatives are effective in nanomolar concentrations, they are attractive as anticancer agents. The compounds disclosed herein can inhibit Tdps in vitro or in vivo. The compounds disclosed herein can inhibit the activity of Tdp1 at nanomolar concentrations both with single and double-stranded DNA substrates.

In addition, disclosed herein are methods of enhancing the antineoplastic effect of topoisomerase 1 (TopI) inhibitors using fluoroquinolone derivatives to inhibit Tdp1 activity, which in turn reduces the ability of Tdp1 to reverse the therapeutic action of TopI inhibitors. For example, it has been discovered that the most potent inhibitor of Tdp1 activity, NF-SDM, acts synergistically with the TopI inhibitor camptothecin to inhibit the growth of the human osteosarcoma cell line U2OS. Thus, also disclosed herein are methods for co-administering the derivatives disclosed herein with another therapeutic agent, particularly an anticancer agent.

As shown below in more detail, only a subset of the tested fluoroquinolone derivatives is effective as Tdp1 inhibitors. The data also shows that those derivatives containing a sulfadimidine moiety or a sulfadiazine moiety have unexpectedly superior Tdp1 inhibitory activity as compared to other fluoroquinolone derivatives that were tested. The ability to inhibit Tdp1 also renders the derivatives unexpectedly synergistic when administered in combination with a topoisomerase I inhibitor (as demonstrated at least with NF-SDM).

In certain embodiments, the subject is identified as being in need of inhibition of Tdp1 activity, and the compound disclosed herein is administered to the identified subject.

Also disclosed herein are methods for treating a Tdp1-related disorder in a subject.

A further embodiment disclosed herein involves the use of a fluoroquinolone derivative in the manufacture of a medicament for treating cancer in a subject.

The fluoroquinolone derivatives also exhibit antineoplastic activity when administered by themselves.

The fluoroquinolone derivatives may have a structure represented by formula 1:

or a pharmaceutically acceptable salt or ester thereof,
wherein $R_1$ is H, alkyl or cycloalkyl;
$R_2$ is H, alkoxy or alkoxyalkyl;
$R_3$ is H or alkyl; and
$R_4$ is wherein each $R^6$ is individually H or alkyl; and a is 3.

In certain embodiments, $R_1$ is cycloalkyl, preferably cyclopropyl; or alkyl, preferably a lower alkyl such as methyl or ethyl. $R_2$ is H or methoxy. $R_3$ is H or a lower alkyl such as methyl.

In certain embodiments, $R_4$ includes a sulfadimidine moiety. In other embodiments, $R_4$ includes a sulfadiazine moiety.

$R_4$ may be, for example, represented by:

wherein each $R^5$ is a lower alkyl, preferably methyl.
$R_4$ may be, for example, represented by:

A list of illustrative fluoroquinolone derivatives is shown in FIG. 1.

The fluoroquinolone derivatives may be synthesized as described in Selvam et al., Synthesis and Antiviral Studies of Novel N-Sulphonamidomethyl piperazinyl Fluoroquinolones, Indian J Pharm Sci 2009; 71(4): 432-436. In general, synthesis of N-sulphonamidomethyl fluoroquinolones derivatives was achieved by stirring an equimolar (0.01 mol) mixture of sulphonamides (sulphonamide, sulphadiazine and sulphadimidine), formaldehyde (37% v/v, ml) and fluoroquinolone (norfloxacin NF, ciprofloxacin CF and gatifloxacin GF) with ethanol using a magnetic stirrer for 3 h. The mixture was allowed to cool over night in a refrigerator. The solid thus obtained was recrystallized from DMF with ethanol.

Sulfonamide Moiety-Containing Compounds

Sulfonamide moiety-containing compounds disclosed herein are also capable of modulating the activity of tyrosyl-DNA phosphodiesterases (Tdps), particularly tyrosyl-DNA phosphodiesterase 1 (Tdp1). It has been determined that compounds that include a sulfonamide moiety, but not a fluoroquinolone as described above, also inhibit Tdp1. However, sulfadimidine by itself (i.e., not coupled to another moiety) does not inhibit Tdp1 as indicated in the Examples below. Thus, although not bound by any theory, it is believed that the sulfonamide moiety is a modulator of Tdp1 inhibition.

Because the sulfonamide moiety-containing compounds are effective in nanomolar concentrations, they are attractive as anticancer agents. The compounds disclosed herein can inhibit Tdps in vitro or in vivo. The compounds disclosed herein can inhibit the activity of Tdp1 at nanomolar concentrations both with single and double-stranded DNA substrates.

In addition, disclosed herein are methods of enhancing the antineoplastic effect of topoisomerase 1 (TopI) inhibitors using sulfonamide moiety-containing compounds to inhibit Tdp1 activity, which in turn reduces the ability of Tdp1 to reverse the therapeutic action of TopI inhibitors. Thus, also disclosed herein are methods for co-administering the sulfonamide moiety-containing compounds disclosed herein with another therapeutic agent, particularly an anticancer agent.

In certain embodiments, the sulfonamide moiety is a sulfadimidine moiety or a sulfadiazine moiety. In certain embodiments, the sulfonamide moiety is coupled to a nitrogen-containing fused heterocyclic moiety (particularly a nitrogen-containing fused aromatic heterocyclic moiety) such as isatin, benzimidazole, isoindole, indole, isoindazole, isoindoline, indoline or purine. In other embodiments, the sulfonamide moiety is coupled to a fluoroquinolone derivative as shown above in formula I. The sulfonamide moiety may be directly coupled to the nitrogen-containing fused heterocyclic moiety via a single or double bond, or they may be coupled via an aliphatic divalent linker such as methylene (—$CH_2$—).

In certain embodiments, the sulfonamide moiety-containing compound, or a pharmaceutically acceptable salt or ester thereof, has a structure represented by formula II:

wherein $R^{10}$ is a nitrogen-containing fused heterocyclic moiety (particularly a nitrogen-containing fused aromatic heterocyclic moiety) such as isatin, benzimidazole, isoindole, indole, isoindazole, isoindoline, indoline or purine;
$R^{11}$ is H or an alkyl, particularly a lower alkyl;
c is 0 or 1;
each $R^{12}$ is individually H or alkyl;
a is 3; and
the dotted line signifies a double bond when c is 0.

$R^{10}$ may be directly coupled to $N(R^{11})$ via a single or double bond, or $R^{10}$ may be coupled to $N(R^{11})$ via an aliphatic divalent linker such as methylene (—$CH_2$—).

In particular, $R^{10}$ is selected from isatin, which may be unsubstituted or substituted, or benzimidazole, which may be unsubstituted or substituted. In particular, $R^{11}$ is H. In particular, at least one $R^{12}$ is lower alkyl.

In a specific embodiment, the sulfonamide moiety-containing compound, or a pharmaceutically acceptable salt or ester thereof, has a structure represented by formula III:

wherein $R^{10}$, $R^{11}$ and c are the same as in formula II, and $R^{13}$ is each individually selected from an alkyl, particularly a lower alkyl such as methyl. In preferred embodiments, each $R^{13}$ is a methyl meaning that the sulfonamide moiety is a sulfadimidine moiety.

In certain embodiments of formulae II or III, $R^{10}$ is a substituted isatin. For example, the sulfadimidine moiety-containing compound, or a pharmaceutically acceptable salt or ester thereof, may have a structure represented by formula IV:

wherein $R^{14}$ and $R^{15}$ are each individually H, halogen; alkyl (particularly lower alkyl); a carbonyl-containing group such as carboxylate, carboxylic acid, acetyl, acetoxy, benzoyl, or benzoxy; an aryl; an aralkyl; an alkylaryl; a halogenated alkyl; a heterocycloalkyl, or a heteroaryl. In certain embodiments, $R^{15}$ is a halogen or a lower alkyl and $R^{14}$ is H. In other embodiments, $R^{15}$ is H and $R^{14}$ is acetyl, benzoyl, or a piperazinyl.

In other embodiments of formulae II or III, $R^{10}$ is a substituted or unsubstituted benzimidazole moiety.

Illustrative sulfadimidine moiety-containing compounds include:

referred to herein as "BDS", and referred to herein as "SPIII-5Cl".

The sulfonamide moiety-containing compounds may be synthesized as described in Selvam et al., Antiviral Chemistry & Chemotherapy 17:107-110 (2006) and Selvam et al, Antiviral Chemistry & Chemotherapy 17:269-274 (2006).

Methods of Treatment and Pharmaceutical Compositions

As described above, the fluoroquinolone and sulfonamide moiety-containing compounds can be used for treating neoplasms (e.g., cancer). Tumors or neoplasms include new growths of tissue in which the multiplication of cells is uncontrolled and progressive. Some such growths are benign, but others are termed "malignant," leading to death of the organism. Malignant neoplasms or "cancers" are distinguished from benign growths in that, in addition to exhibiting aggressive cellular proliferation, they invade surrounding tissues and metastasize. Moreover, malignant neoplasms are characterized in that they show a greater loss of differentiation (greater "dedifferentiation"), and of their organization relative to one another and their surrounding tissues. This property is also called "anaplasia."

Neoplasms treatable by the presently disclosed compounds include all solid tumors, i.e., carcinomas and sarcomas, including Kaposi's sarcoma. Carcinomas include those malignant neoplasms derived from epithelial cells which tend to infiltrate (invade) the surrounding tissues and give rise to metastases. Adenocarcinomas are carcinomas derived from glandular tissue or in which the tumor cells form recognizable glandular structures. Sarcoma, including Kaposi's sarcoma broadly include tumors whose cells are embedded in a fibrillar or homogeneous substance like embryonic connective tissue.

Treatable cancers include, for example, colon cancer, bladder cancer, breast cancer, melanoma, ovarian carcinoma, prostatic carcinoma, or lung cancer, and a variety of other cancers as well. The compounds may be especially useful in the inhibition of cancer growth in adenocarcinomas, including, for example, those of the prostate, breast, kidney, ovary, testes, and colon. The compounds are further useful against melanomas, which derive from the melanocyte system in the skin and other organs.

A solid tumor can be malignant, e.g. tending to metastasize and being life threatening, or benign. Examples of solid tumors that can be treated according to a method of the present invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synoviona, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Moreover, tumors comprising dysproliferative changes (such as metaplasias and dysplasias) are treated or prevented in epithelial tissues such as those in the cervix, esophagus, and lung. Thus, the presently disclosed methods provide for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, Medicine, 2d Ed., J. B. Lippincott Co., Philadelphia.

In certain embodiments, the presently disclosed methods are directed to a method for inhibiting cancer growth, including processes of cellular proliferation, invasiveness, and metastasis in biological systems. The method includes the use of a fluoroquinolone compound as an inhibitor of cancer growth. Preferably, the method is employed to inhibit or reduce cancer cell proliferation, invasiveness, metastasis, or tumor incidence in living animals, such as mammals.

Also provided herein is a method of inducing cytotoxicity (cell killing) in cancer cells or reducing the viability of cancer cells. For example, the fluoroquinolone and sulfonamide moiety-containing compounds can be used to induce cytotoxicity in cells of carcinomas of the prostate, breast, ovary, testis, lung, colon, or breast. The selective killing of the cancer cells can occur through apoptosis, necrosis, another mechanism, or a combination of mechanisms.

The killing of cancer cells can occur with less cytotoxicity to normal cells or tissues than is found with conventional cytotoxic therapeutics, preferably without substantial cytotoxicity to normal cells or tissues. For example, the fluoroquinolone and sulfonamide moiety-containing compounds identified herein can induce cytotoxicity in cancer cells while producing little or substantially no cytotoxicity in normal cells. Thus, unlike conventional cytotoxic anticancer therapeutics, which typically kill all growing cells, the fluoroquinolones and sulfonamide moiety-containing compounds can produce differential cytotoxicity: tumor cells are selectively killed whereas normal cells are spared. Thus, in another embodiment, there is disclosed a method for inducing differential cytotoxicity in cancer cells relative to normal cells or tissue. This differential in cytotoxicity associated with the fluoroquinolone and sulfonamide moiety-containing compounds occurs as a result of apoptosis, necrosis, another mechanism, or a combination of such mechanisms.

The fluoroquinolone and sulfonamide moiety-containing compounds exhibit their cancer treatment properties at concentrations that lead to fewer side effects than those of known chemotherapeutic agents, and in some cases are substantially free of side effects. The fluoroquinolone and sulfonamide moiety-containing compounds are useful for extended treatment protocols, where other compounds would exhibit undesirable side-effects. In addition, it is believed that the properties of hydrophilicity and hydrophobicity are well balanced in these compounds, enhancing their utility both in vitro and especially in vivo, while other compounds lacking such balance are of substantially less utility. Specifically, the compounds have an appropriate degree of solubility in aqueous media to permit absorption and bioavailability in the body, while also having a degree of solubility in lipids to permit traversal of the cell membrane to a putative site of action. The compounds are maximally effective if they can be delivered to the site of the tumor and are able to enter the tumor cells.

In the treatment of certain localized cancers, the degree of hydrophilicity of the fluoroquinolone or sulfonamide moiety-containing compound can be of lesser importance. The fluoroquinolone and sulfonamide moiety-containing compounds which may have low solubility in aqueous systems, can be used in direct or topical treatment of skin cancers, e.g., melanoma or basal cell carcinoma, or by implantation into the brain to topically treat brain cancer.

The fluoroquinolone and sulfonamide moiety-containing compounds are effective to inhibit the proliferation, invasiveness, or metastasis of cancer cells in vitro, as well as in vivo. These compounds possess an excellent balance of properties, in that they are shown to possess unusually strong activity in inhibiting the cancer growth, including proliferation, invasiveness, or metastasis of cancer cells.

Human cancers are characterized by genomic instability, which leads to the accumulation of DNA lesions. Hence, tumor cells are highly dependent on normal repair for survival.

Tdp1 Inhibition

Tdp1 is a member of the phospholipase D superfamily, which encompasses a diverse group of enzymes that catalyze phosphodiester bond cleavage on substrates ranging from phospholipids to DNA, or in the case of Tdp1, protein-DNA complexes. The majority of the sequence identity between Tdp1 and the members of the PLD family is restricted to two copies of an active site signature motif $H(X)K(X_4)D$, also referred to as an HKD motif, which has been implicated in the catalytic mechanism of these enzymes. Two such motifs are present in the N- and C-terminal domains of human Tdp1, both of which contain the conserved histidine and lysine residues ($^{263}HTK^{265}$ and $^{495}HIK^{497}$) but lack the aspartate residues that exist in other HKD motifs. Thus, it has been suggested that Tdp1 represents a distinct subclass of the PLD superfamily based on its unique "HKN" motifs. The importance of the two signature HKN motifs for Tdp1 enzymatic activity has been established by site-directed mutagenesis. Indeed, mutation of H263 produces a catalytically inactive enzyme, whereas mutating H495, K265, or K497 results in impaired enzymatic activity (Interthal, H., et al. Proc Natl Acad Sci USA, 2001, 98. 12009; Raymond, A. C., et al. J Mol Biol, 2004, 338. 895). These results are consistent with studies performed on other members of the PLD family (Gottlin, E. B., et al. Proc Natl Acad Sci USA, 1998, 95. 9202; Xie, Z., et al. J Biol Chem, 2000, 275. 24962).

The affiliation of Tdp1 with the PLD superfamily has been further established through comparative analysis of the three-dimensional structure of the catalytically active N-terminal truncated human Tdp1 (Δ1-148) (Davies, D. R., Interthal, H., Champoux, J. J., and HoI, W. G. Structure, 2002, 10. 237) with the known crystal structures of two members of the PLD superfamily, a PLD from *Streptomyces* and a bacterial nuclease from *Salmonella tryphimurium*. Albeit the low sequence identity amid these three enzymes, they share a strikingly similar tertiary structure. In addition, the superimposition of the active sites supports the notion that all three enzymes participate in analogous reaction chemistry. The crystallographic studies of human Tdp1 reveals a monomelic structure comprised of two topologically similar α-β-α domains. Each domain contributes a histidine and lysine residue to form the active site, which is centrally located at the pseudo-twofold axis of symmetry between the two domains. The Tdp1 crystal structure also reveals that four additional residues, which are conserved in all Tdp1 orthologs, N283, Q294, N516, and E538, are also positioned near the active site (Davies, D. R., Interthal, H., Champoux, J. J., and HoI, W. G. Structure, 2002, 10. 237).

In order to gain further insight into the substrate binding properties and catalytic mechanism of Tdp1, co-crystal structures were solved of human Tdp1 bound to vanadate (Davies, D. R., Interthal, H., Champoux, J. J., and HoI, W. G. J Mol Biol, 2002, 324. 917; Davies, D. R., Interthal, H., Champoux, J. J., and HoI, W. G. Chem Biol, 2003, 10. 139) an oxyanion form of pentavalent vanadium. Unlike the phosphate ion, vanadate can form five-coordinate species allowing it to serve as a transition state analogue and eliminate enzyme turnover. Initial examination of the quaternary structure revealed an asymmetrical substrate-binding channel that extended in opposite directions from the active site across the entire surface of Tdp1. The DNA moiety bound to one side of the active site in a relatively narrow cleft that is predominantly positively charged. Conversely, the peptide moiety bound to the other side of the active site in a relatively large, more open cleft that contains a mixed charge distribution. Interestingly, the DNA-binding groove is highly conserved among Tdp1 orthologues, while the peptide-binding pocket shows much less sequence conservation between different species (Davies, D. R., Interthal, H., Champoux, J. J., and HoI, W. G. Chem Biol, 2003, 10. 139; Davies, D. R., Interthal, H., Champoux, J. J., and HoI, W. G. J Med Chem, 2004, 47. 829).

A closer look into the active site of the quaternary structure shows that the vanadate ion exhibits trigonal bipyramidal geometry, which is consistent with a transition state of an $S_N2$ nucleophilic attack on phosphate. The apical coordination to the vanadate molecule is filled by the imidazole Nε2 atom of the active site H263 residue of Tdp1 and the oxygen atom of the tyrosine side chain of the Top1-derived peptide, whereas the 3'-hydroxyl of the DNA oligonucleotide occupies one of the three equatorial positions. The remaining two equatorial oxygens, which represent the nonbridging oxygens of the phosphodi ester substrate, form hydrogen bonds with the amino groups of K265 and K495. It is well-recognized that the incoming and outgoing groups in an $S_N2$ reaction occupy the two axial positions of a trigonal bipyramid. Therefore, it is evident from the Tdp1-vanadate structure that the first step in the Tdp1 catalytic mechanism involves the nucleophilic attack of the phosphotyrosyl bond by the H263 residue from the N-terminal HKN motif Additionally, the H493 residue from the C-terminal HKN motif acts as a general acid and donates a proton to the apical tyrosine-containing peptide-leaving group. This results in the formation of a transient covalent phosphoamide bond between the Nε2 atom of H263 and the 3'-end of the DNA. Hydrolysis of this covalent intermediate is proposed to be carried out by a water molecule that is activated by the H493 residue acting as a general base. The second $S_N2$ reaction step in the Tdp1 catalytic mechanism is supported by in vitro biochemical studies with the SCAN1 H493R mutant, which leads to an accumulation of Tdp1-DNA covalent intermediate. Overall, the final product released after Tdp1 catalysis is a DNA molecule with a 3'-phosphate end.

A stalled Topi-DNA complex is an unmanageable substrate for Tdp1 because of the limited access of the scissile phosphotyrosyl bond, which is internally located within the Top1-DNA complex (Redinbo, M. R., Stewart, L., Kuhn, P., Champoux, J. J., and HoI, W. G. Science, 1998, 279. 1504).

This statement is corroborated by the poor processing by Tdp1 of a suicide complex made of full-length human Top1 covalently linked to a DNA oligonucleotide (Debethune, L., Kohlhagen, G., Grandas, A., and Pommier, Y. Nucleic Acids Res, 2002, 30. 1 198). Prior denaturation of the Topi-DNA complex, which presumably results in enhanced steric access of the phosphotyrosyl bond, is required for Tdp1 enzymatic activity toward a full-length Top1-DNA covalent complex (Yang, S. W., Burgin, A. B., Jr., Huizenga, B. N., Robertson, C. A., Yao, K. C., and Nash, H. A. Proc Natl Acad Sci USA, 1996, 93. 1 1534). Thus, it has been suggested that the Topi must undergo proteolysis in order for efficient Tdp1 activity (Yang, S. W., Burgin, A. B., Jr., Huizenga, B. N., Robertson, C. A., Yao, K. C., and Nash, H. A. Proc Natl Acad Sci USA, 1996, 93. 11534; Davies, D. R., Interthal, H., Champoux, J. J., and Hol, W. G. Chem Biol, 2003, 10. 139; Debethune, L., Kohlhagen, G., Grandas, A., and Pommier, Y. Nucleic Acids Res, 2002, 30. 1198), which is in agreement with studies demonstrating that the effectiveness of Tdp1 processing decreases as the length of the Top1 polypeptide is extended (Debethune, L., Kohlhagen, G., Grandas, A., and Pommier, Y. Nucleic Acids Res, 2002, 30. 1198). Accordingly, several studies have shown that Top1 is degraded in some cells lines following CPT treatment, suggesting that Top1 ubiquitination and degradation contribute to CPT resistance (Beidler, D. R., and Cheng, Y. C. Mol Pharmacol, 1995, 47. 907; Desai, S. D., Li, T. K., Rodriguez-Bauman, A., Rubin, E. H., and Liu, L. F. Cancer Res, 2001, 61. 5926; Desai, S. D., Liu, L. F., Vazquez-Abad, D., and D'Arpa, P. J Biol Chem, 1997, 272. 24159; Zhang, H. F., Tomida, A., Koshimizu, R., Ogiso, Y., Lei, S., and Tsuruo, T. Cancer Res, 2004, 64. 1 114). In addition, prevention of Top1 degradation by the proteasome inhibitors, MG132 or PS-341, results in increased sensitivity to CPT. These studies imply that Top1 degradation via a ubiquitin-proteasome pathway may play a role in the repair of Top1-mediated damage, wherein Top1 degradation serves to prepare the Top1 cleavage complexes for hydrolysis by Tdp1.

Besides the physiological substrates, numerous synthetic Tdp1 substrates have been identified. Specifically, phosphotyrosine analogues, such as 3'-(4-nitro)phenol and 3'(4-methyl)phenol, have been used in kinetic analysis of the Tdp1 catalytic mechanism. Other artificial substrates include a 3'-linker-biotin (Interthal, H., Chen, H J., and Champoux, J J. J Biol Chem, 2005, 280. 36518) and a fluorescent 3'-4-methylumbelliferone (Nitiss, K. C., Malik, M., He, X., White, S. W., and Nitiss, J. L. Proc Natl Acad Sci USA, 2006, 103. 8953), which could potentially be employed in high-throughput screens for Tdp1 inhibitors, similar to how the 3'-BV tag has been used (discussed below).

The 3'-phosphate-end generated by Tdp1 must be hydrolyzed to a 3'-hydroxyl in order for further DNA repair to occur. Polynucleotide kinase phosphatase (PNKP), a bifunctional enzyme with 5'-kinase and 3'-phosphatase activities, has been suggested as a reasonable candidate in human cells for the repair of these 3'-phosphate lesions. In vitro studies have shown that T4 kinase, the bacteriophage equivalent of PNKP, can hydrolyze the resulting 3'-phosphate produced by Tdp1 (Yang, S. W., Burgin, A. B., Jr., Huizenga, B. N., Robertson, C. A., Yao, K. C, and Nash, Y L. A. Proc Natl Acad Sci USA, 1996, 93. 11534). It has also been shown that human A549 cells that are defective in PNKP accrue similar levels of CPT-induced strand breaks in comparison to SCAN1 cells (El-Khamisy, S. F., Saifi, G. M., Weinfeld, M., Johansson, F., Helleday, T., Lupski, J. R., and Caldecott, K. W. Nature, 2005, 434. 108), which suggested that Tdp1 and PNKP function in the same repair pathway in human cells. Furthermore, PNKP is known to interact with the XRCC1 protein, which together with the other base excision repair (BER) proteins, such as DNA polymerase β, DNA ligase III, and poly(ADP-ribose) polymerase 1(P ARP-I) forms a multiprotein DNA repair complex (Whitehouse, C J., Taylor, R. M., Thistlethwaite, A., Zhang, H., Karimi-Busheri, F., Lasko, D. D., Weinfeld, M., and Caldecott, K. W. Cell, 2001, 104. 107). Recently, Tdp1 has also been shown to be a member of the BER repair complex through interactions with DNA ligase III (El-Khamisy, S. F., Saifi, G. M., Weinfeld, M., Johansson, F., Helleday, T., Lupski, J. R., and Caldecott, K. W. Nature, 2005, 434. 108) and XRCC1 (Plo, L, Liao, Z. Y., Barcelo, J. M., Kohlhagen, G., Caldecott, K. W., Weinfeld, M., and Pommier, Y. DNA Repair (Amst), 2003, 2. 1087). XRCC1-deficient cells have been discovered to be hypersensitive to CPT and defective in Tdp1 activity, which is in agreement with a direct role of Tdp1 in association with the BER complex for the removal and repair of Top1-mediated DNA damage. In addition, the interaction of XRCC1 with PNKP has been shown to stimulate both the 5'-kinase and 3'-phosphatase activities of this enzyme (Whitehouse, C. J., Taylor, R. M., Thistlethwaite, A., Zhang, H., Karimi-Busheri, F., Lasko, D. D., Weinfeld, M., and Caldecott, K. W. Cell, 2001, 104. 107). Similarly, XRCC1 interacts with DNA ligase III and increases the intracellular stability of the ligase (Caldecott, K. W., Tucker, J. D., Stanker, L. H., and Thompson, L. H. Nucleic Acids Res, 1995, 23. 4836; Taylor, R. M., Wickstead, B., Cronin, S., and Caldecott, K. W. Cur r Biol, 1998, 8. 877). The association PARP-I with the XRCC1 complex has also been observed. However, its function in the repair of Top1-mediated DNA damage remains to be determined. PARP-I is a nuclear enzyme often termed a molecular nick sensor, which recognizes and binds to DNA single or double strand breaks. Indeed, the hypersensitivity of PARP-I-deficient cells to CPT has been shown to be directly related to a functional defect in Tdp1 (Pommier, Y., Barcelo, J. M., Rao, V. A., Sordet, O., Jobson, A. G., Thibaut, L., Miao, Z. H., Seiler, J. A., Zhang, H., Marchand, C, Agama, K., Nitiss, J. L., and Redon, C. Prog Nucleic Acid Res Mol Biol, 2006, 81. 179), which suggests that PARP-1 may be involved in the targeting of a BER complex to sites of Top1-mediated DNA damage. The effects on Tdp1 activity after the association with the XRCC1 complex are still unresolved. However, based on these observations and several others, a scheme for the role of the XRCC1 repair complexes in the repair of Topi-mediated DNA lesions has been proposed. Following degradation or denaturation of Topi to expose the phosphotyrosyl linkage, Tdp1 hydrolyzes the Top1-DNA bond. Next, PNKP hydrolyzes the resulting 3'-phosphate end and catalyzes the phosphorylation of the 5'-end of the DNA. Lastly, DNA polymerase β replaces the missing DNA segment and DNA ligase III reseals the DNA.

Figure 4:
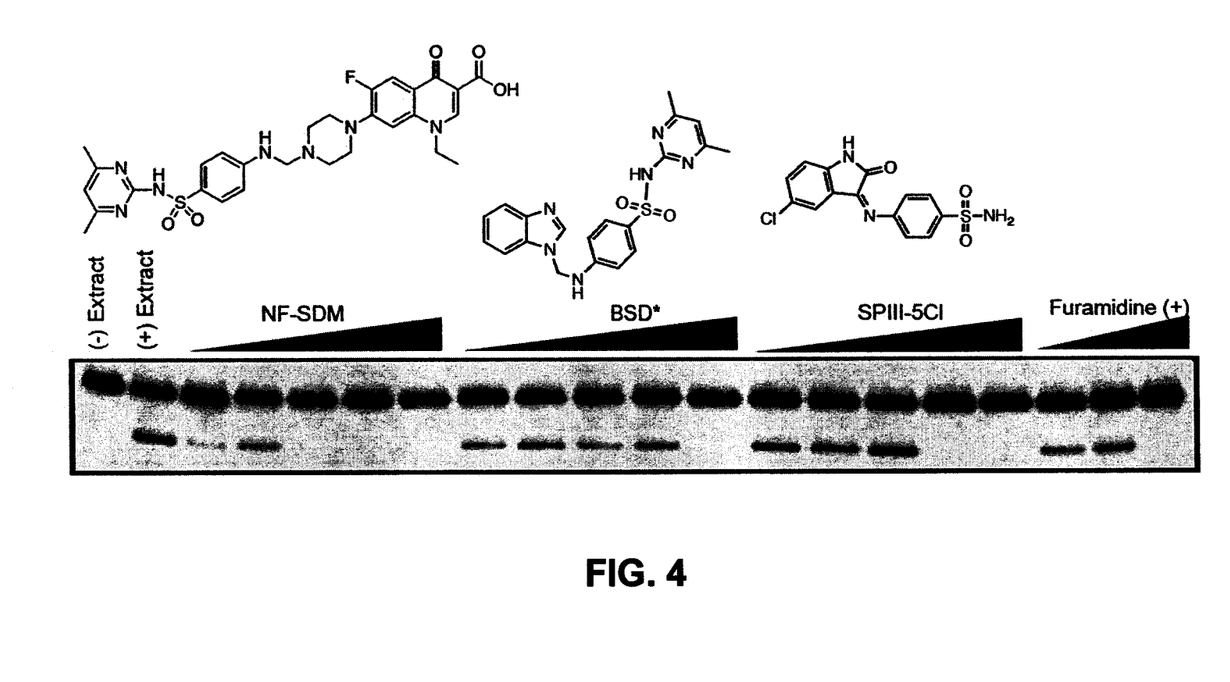
FIG. 4 shows the chemical structures of three sulfadimidine moiety-containing compounds and phosphorimager pictures of the dose response inhibition of Tdp1 by these compounds.

The initial understanding of the role of Tdp1 in DNA repair and the rationale for targeting Tdp1 for anticancer therapy in combination with CPT came about by taking advantage of the genetic manipulations possible in yeast. Tdp1 is one of several potentially redundant pathways involved in the repair of Top-mediated damage in yeast (Pouliot, J. J., Robertson, C. A., and Nash, H. A. Genes Cells, 2001, 6. 677; Pommier, Y., Barcelo, J. M., Rao, V. A., Sordet, O., Jobson, A. G., Thibaut, L., Miao, Z. H., Seiler, J. A., Zhang, H., Marchand, C, Agama, K., Nitiss, J. L., and Redon, C. Prog Nucleic Acid Res Mol Biol, 2006, 81. 179; Deng, C, Brown, J. A., You, D., and Brown, J. M. Genetics, 2005, 170. 591; Liu, C, Pouliot, J J., and Nash, H. A. Proc Natl Acad Sd USA, 2002, 99. 14970; Liu, C, Pouliot, J. J., and Nash, H. A. DNA Repair (Amst), 2004, 3. 593; Vance, J. R., and Wilson, T. E. Proc Natl Acad Sci USA, 2002, 99. 13669). This has been demonstrated through the observation that significant increases in sensitivity to CPT in TDP 1-defective yeast are conditional upon at least one additional mutation in other DNA repair and checkpoint genes. For instance, hypersensitivity to CPT is observed when TDP1 and the checkpoint gene Rad9 are simultaneously inactivated. In addition, a second group of conditional genes are the three sets of genes implicated in the structure-specific endonuclease repair pathways. RadllRadlO (XPFIERCCl) functions primarily in the nucleotide excision repair pathway, where it cleaves on the 5'-side of the repair bubble formed around bulky DNA lesions (Vance, J. R., and Wilson, T. E. Proc Natl Acad Sci USA, 2002, 99. 13669; Roberts, J. A., and White, M. F. Nucleic Acids Res, 2005, 33. 6662; Bardwell, A. J., Bardwell, L., Tomkinson, A. E., and Friedberg, E. C. Science, 1994, 265. 2082). Mus81IMms4 {Mus81IEmel) and MrelllRad50IXrs2 (MrelllRad50INbs1) cleave a 3'-flap upstream of a branch point [68, 69] and function independently from the Tdp1 pathway (FIG. 4A) (Deng, C, Brown, J. A., You, D., and Brown, J. M. Genetics, 2005, 170. 591; Liu, C, Pouliot, J. J., and Nash, H. A. Proc Natl Acad Sci USA, 2002, 99. 14970). Mutations in each of these genes render TDP1-deficient yeast cells highly sensitive to CPT. Specific homologues for each of the genes mentioned above are present in humans (shown in parentheses), with the exception of Rad9.

In humans, there is no single Rad9 orthologue readily identifiable, but rather a family of tandem BRCT domain-containing proteins that act in the checkpoint response. Some of the Rad9 human orthologues include BRCAl, 53BP 1, and MDCl, which are commonly referred to as checkpoint mediators. Based on the insight gained from yeast, it has been proposed that there are two redundant pathways involved in repairing Topi-mediated DNA damage in humans. The first is a Tdp1-dependent pathway involving collaboration with the previously mentioned XRCCl complex. The second is a Tdp1-independent, checkpoint-dependent pathway involving the Rad9 human homologues in the checkpoint response and the removal of damage by the three parallel functioning endonucleases. Even though there is redundancy in the repair of Top1-mediated DNA damage, it may not be critical to the clinical relevance of Tdp1 inhibition, since it is well established that deficiencies in checkpoint mechanisms are a common feature in cancer cells (Dasika, G. K., Lin, S. C, Zhao, S., Sung, P., Tomkinson, A., and Lee, E. Y. Oncogene, 1999, 18. 7883). For example, if cancer-related checkpoint inactivation arises, then Tdp1 becomes the principle source for the removal of Top1-mediated DNA damage.

DNA topoisomerase I (Top1) is ubiquitous and essential in higher eukaryotes. It relieves DNA torsional stress and relaxes DNA supercoiling by introducing DNA single-strand breaks. Top1 can be trapped by DNA lesions that accumulate in cancer cells. Top1 is also the target of the anticancer agent camptothecin and non-camptothecin inhibitors. Top1 inhibitors damage DNA by trapping covalent complexes between the Top1 catalytic tyrosine and the 3'-end of the broken DNA. Tyrosyl-DNA phosphodiesterase (Tdp1) repairs Top1-DNA covalent complexes by hydrolyzing the tyrosyl-DNA bond.

Tdp1 inhibitors are therefore useful as anticancer agents both in monotherapy and in combination with other anticancer compounds (particularly DNA-targeted anticancer compounds) such as Top1 inhibitors. Tumor cells, whose repair pathways are commonly deficient, might be selectively sensitized to Top1 inhibitors compared to normal cells that contain redundant repair pathways. Moreover, Tdp1 inhibitors are effective by themselves as anticancer agents as oncogenic activation tends to increase free radical production and genomic instability (Cerutti P A (1985) Science 227 (4685): 375-381; Kc S et al. Mutat Res. (2006) 29 593(1-2):64-79; Vafa et al., Mol Cell 9(5): 1031-1044 (2002)).

Thus, disclosed herein are methods for treating cancer and other cell proliferative disorders by administering to a subject in need thereof an effective amount of a combination of a (i) fluoroquinolone compound or (ii) a sulfonamide moiety-containing compound, together with a Top1 inhibitor. A variety of Top1 inhibitors have been reported, including camptothecin, irinotecan, topotecan, saintopin, and derivatives and analogs thereof. In another aspect, disclosed herein are pharmaceutical compositions including (i) a fluoroquinolone compound or (ii) a sulfonamide moiety-containing compound together with a Topi inhibitor, optionally including a pharmaceutically-acceptable carrier or excipient.

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, crosslinking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly (epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, transepidemial, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

EXAMPLES

5'-$^{32}$P-labeled DNA substrate (1 nmol/L; N14Y; 5'-GATCTAAAAGACTT-pY-3') was incubated with 0.2 nmol/L recombinant Tdp1 in the absence or presence of inhibitor for 15 min at room temperature in an assay buffer containing 1×PBS, pH 7.4, 80 mmol/L KCl and 0.01% Tween-20. Reactions were terminated by the addition of 1 volume of gel loading buffer [99.5% (v/v) formamide, 5 mmol/L EDTA, 0.01% (w/v) xylene cyanol, and 0.01% (w/v) bromophenol blue]. Samples were subjected to a 16% denaturing PAGE and gels were exposed after drying to a PhosphorImager screen (GE Healthcare). Gel images were scanned using a Typhoon 8600 (GE Healthcare) and densitometric analyses were performed using the ImageQuant software package (GE Healthcare).

Figure 2:
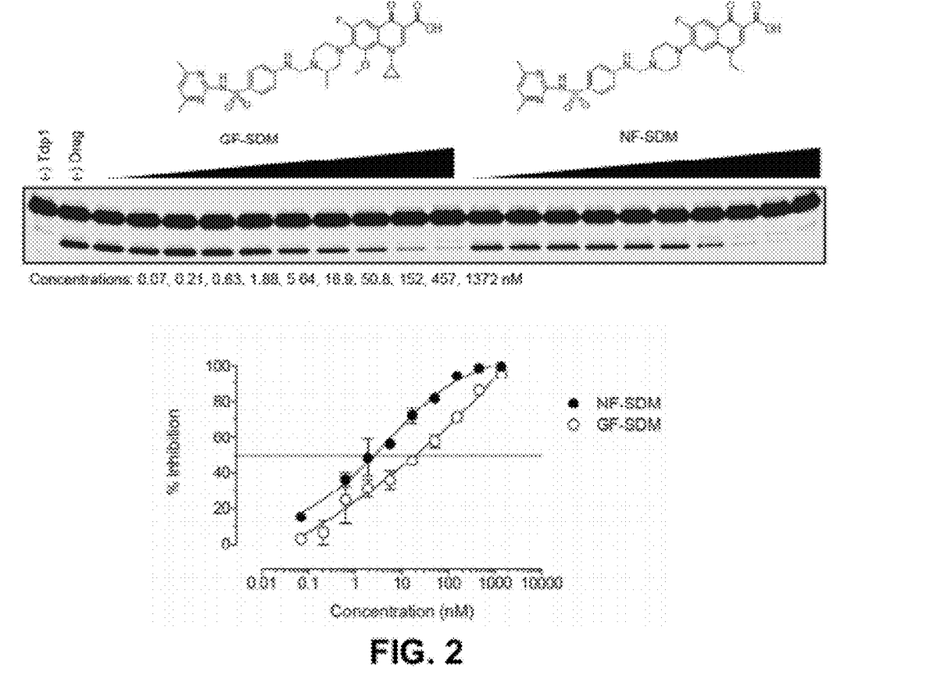
FIG. 2. The upper panel shows the chemical structure of the two most potent fluoroquinolone inhibitors and phosphorimager pictures of the dose response inhibition of Tdp1 by these compounds. The lower panel depicts inhibition curves derived from four independent experiments.

Two sulfadimidine-containing fluoroquinolone derivatives of norfloxacin and gatifloxacin (NF-SDM & GF-SDM, respectively) were prepared and shown to inhibit Tdp1 catalytic activity at 5 and 22 nM, respectively (FIGS. 1 and 2). The antibiotic scaffolds norfloxacin and gatifloxacin or the sulfadimidine portion of the molecules were unable to inhibit Tdp1 by themselves at concentrations up to 333 µM (FIG. 1 and data not shown). The compounds containing sulfadimidine moieties (SDM) were more potent than the one containing a sulfadiazine moiety (SD), whereas the derivatives containing only the 4-amino benzene sulfonamide moiety were inactive up to 333 µM (FIG. 1). The results for BSD and SPIII-5Cl are shown in FIG. 4.

U2OS cells (Developmental Therapeutics Program, NCI) were plated at $3\times10^3$ cells in a total volume of 100 µl per well in a 96 well plate and incubated at 37° C./5% $CO_2$ for 24 hours prior to drug treatment. CPT and another drug of interest (both in DMSO stock solution) were prepared at double the desired concentration, and serially diluted in cells' media. After medium was aspirated off cells, 50 µl of CPT was plated down each column at four-fold dilutions in subsequent columns and 50 µl of another drug of interest was plated across rows, at two-fold dilutions in subsequent rows. A single drug dose response was also included for each drug tested, to which 50 µl of regular media was added to reconstitute a final volume of 100 µl in each well. Plates were further incubated for 72 hours and proliferation was assayed by adding 20 µl of 3-(4,5-dimethylthiazol-2-yl)-5-(3 carboxymethoxyphenyl)-2-(4-sulfophenyl)-2H-tetrazolium (MTS) Cell Titer Reagent (Promega) to each well. Plates were lightly mixed and placed back into the incubator until the appropriate color change occurred (~1 hr), at which point plates were read on a Molecular Device Gemini fluorescence plate reader at an absorbance of 490 nm for cell viability. Raw data were plotted using GraphPad Prism and compared to each sample's control (GraphPad Software Inc.).

Figure 3:
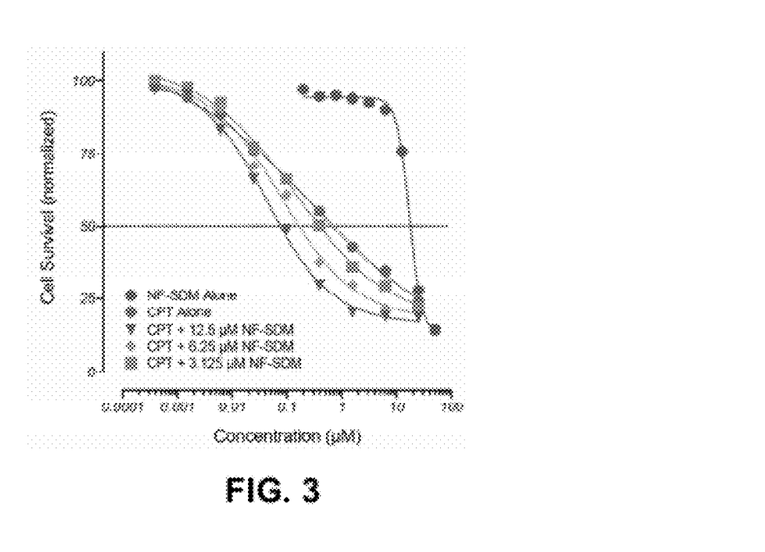
FIG. 3 is a graph of the results of a cytotoxicity assay in the presence of camptothecin and/or NF-SDM (a fluoroquinolone Tdp1 inhibitor). The increase of the curve slope when NF-SDM concentration is raised indicates a synergistic effect of NF-SDM with CPT.

The most potent fluoroquinolone inhibitor, NF-SDM, was tested on human osteosarcoma U2OS cells for synergy with the Top1 poison camptothecin (CPT). It was found to synergize with CPT at 3, 6 and 12 µM concentrations (FIG. 3).

Certain specific embodiments are disclosed below with reference to numbered paragraphs:

1. A method for treating cancer in a subject, comprising administering to a subject having cancer a therapeutically effective amount of a topoisomerase I (TopI) inhibitor and a therapeutically effective amount of a fluoroquinolone derivative that inhibits tyrosyl-DNA-phosphodiesterase 1 (Tdp1) activity, thereby treating the cancer in the subject.

2. A method for treating cancer in a subject, comprising administering to a subject having cancer a therapeutically effective amount of a fluoroquinolone derivative that inhibits tyrosyl-DNA-phosphodiesterase 1 (Tdp1) activity, thereby treating the cancer in the subject.

3. A method for inhibiting tyrosyl-DNA-phosphodiesterase 1 (Tdp1) activity in a biological sample with Tdp1 activity, comprising contacting the biological sample with a fluoroquinolone derivative that inhibits Tdp1 activity, thereby inhibiting Tdp1 activity.

4. The method of any one of paragraphs 1 to 3, wherein the fluoroquinolone derivative comprises:

or a pharmaceutically acceptable salt or ester thereof, wherein $R_1$ is H, alkyl or cycloalkyl;

$R_2$ is H, alkoxy or alkoxyalkyl;

$R_3$ is H or alkyl; and $R_4$ is wherein each $R^6$ is individually H or alkyl; and a is 3.

5. The method of paragraph 4, wherein $R_1$ is cyclopropyl or ethyl.

6. The method of paragraph 4 or 5, wherein $R_2$ is H or methoxy.

7. The method of any one of paragraphs 4 to 6, wherein $R_3$ is H or methyl.

8. The method of any one of paragraphs 4 to 7, wherein $R_4$ is wherein each $R^5$ is individually alkyl.

9. The method of paragraph 8, wherein each $R^5$ is methyl.

10. The method of any one of paragraphs 4 to 7, wherein $R_4$ is

11. The method of paragraph 4, wherein:
$R_1$ is cyclopropyl, $R_2$ is methoxy, $R_3$ is methyl, and $R_4$ is wherein each $R^5$ is methyl.

12. The method of paragraph 4, wherein $R_1$ is ethyl, $R_2$ is H, $R_3$ is H, and $R_4$ is 13. The method of any one of paragraphs 1 or 4 to 12, wherein the TopI inhibitor comprises a camptothecin.

14. The method of any one of paragraphs 1, 2 or 4 to 13, wherein the cancer is selected from fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, or retinoblastoma.

15. The method of any one of paragraphs 1, 2 or 4 to 13, wherein the cancer is colon cancer.

16. The method of any one of paragraphs 1, 2 or 4 to 13, wherein the cancer is human osteosarcoma.

17. A pharmaceutical composition, comprising a therapeutically effective amount of a TopI inhibitor and a therapeutically effective amount of a fluoroquinolone derivative that inhibits Tdp1 activity.

18. The pharmaceutical composition of paragraph 17, wherein the fluoroquinolone derivative comprises:

or a pharmaceutically acceptable salt or ester thereof,
wherein R₁ is H, alkyl or cycloalkyl;
R₂ is H, alkoxy or alkoxyalkyl;
R₃ is H or alkyl; and
R₄ is wherein each R⁶ is individually H or alkyl; and a is 3.

19. The pharmaceutical composition of paragraph 18, wherein R₁ is cyclopropyl or ethyl.

20. The pharmaceutical composition of claim 18 or 19, wherein R₂ is H or methoxy.

21. The pharmaceutical composition of any one of paragraphs 18 to 20, wherein R₃ is H or methyl.

22. The pharmaceutical composition of any one of paragraph 18 to 21, wherein R₄ is wherein each R⁵ is individually alkyl.

23. The pharmaceutical composition of paragraph 22, wherein each R⁵ is methyl.

24. The pharmaceutical composition of any one of paragraphs 18 to 21, wherein R₄ is 25. The pharmaceutical composition of paragraph 18, wherein:
R₁ is cyclopropyl, R₂ is methoxy, R₃ is methyl, and R₄ is wherein each R⁵ is methyl.

26. The pharmaceutical composition of paragraph 18, wherein R₁ is ethyl, R₂ is H, R₃ is H, and R₄ is 27. The pharmaceutical composition of any one of paragraphs 17 to 26, wherein the TopI inhibitor comprises a camptothecin.

In view of the many possible embodiments to which the principles of the disclosed invention may be applied, it should be recognized that the illustrated embodiments are only preferred examples of the invention and should not be taken as limiting the scope of the invention.

What is claimed is:

1. A method for treating colon cancer or human osteosarcoma in a subject, comprising administering to a subject having colon cancer or human osteosarcoma a therapeutically effective amount of a topoisomerase I (TopI) inhibitor and a therapeutically effective amount of (i) a fluoroquinolone derivative that inhibits tyrosyl-DNA-phosphodiesterase 1 (Tdp1) activity, thereby treating the colon cancer or human osteosarcoma in the subject, wherein the
TopI inhibitor is selected from camptothecin, irinotecan, topotecan, or saintopin,
and wherein the fluoroquinolone derivative comprises or a pharmaceutically acceptable salt or ester thereof, wherein
(a) R₁ is cyclopropyl, R₂ is methoxy, R₃ is methyl, and R₄ is wherein each R⁵ is methyl; or
(b) R₁ is ethyl, R₂ is H, R₃ is H, and R₄ is wherein each R⁵ is methyl.

2. The method of claim 1, wherein the TopI inhibitor comprises a camptothecin.

3. A pharmaceutical composition, comprising a therapeutically effective amount of a TopI inhibitor and a therapeutically effective amount of (i) a fluoroquinolone derivative that inhibits Tdp1 activity, wherein the TopI inhibitor is selected from camptothecin, irinotecan, topotecan, or saintopin, and wherein the fluoroquinolone derivative comprises or a pharmaceutically acceptable salt or ester thereof, wherein (a) $R_1$ is cyclopropyl, $R_2$ is methoxy, $R_3$ is methyl, and $R_4$ is wherein each $R^5$ is methyl; or (b) $R_1$ is ethyl, $R_2$ is H, $R_3$ is H, and $R_4$ is wherein each $R^5$ is methyl.

4. The method of claim 1, wherein the TopI inhibitor comprises topotecan.

5. The method of claim 1, wherein the method is for treating human osteosarcoma.

6. The method of claim 1, wherein the method is for treating colon cancer.

7. The method of claim 1, wherein the fluoroquinolone derivative is compound (a).

8. The method of claim 1, wherein the fluoroquinolone derivative is compound (b).

9. The composition of claim 3, wherein the fluoroquinolone derivative is compound (a).

10. The composition of claim 3, wherein the fluoroquinolone derivative is compound (b).

11. The composition of claim 3, wherein the TopI inhibitor comprises topotecan.

\* \* \* \* \*